US007767698B2

(12) United States Patent
Warchol et al.

(10) Patent No.: US 7,767,698 B2
(45) Date of Patent: Aug. 3, 2010

(54) FORMULATION AND USE THEREOF

(75) Inventors: Mark P. Warchol, Kalamazoo, MI (US); Folke Morén, Limhamn (SE); Kristina Thyresson, Lund (SE); Elisabeth Sthengel, Helsingborg (SE); Sven-Börje Andersson, Okakra (SE)

(73) Assignee: McNeil AB, Helsingborg (SE)

( * ) Notice: Subject to any disclaimer, the term of this patent is extended or adjusted under 35 U.S.C. 154(b) by 752 days.

(21) Appl. No.: 10/453,808

(22) Filed: Jun. 2, 2003

(65) Prior Publication Data

US 2004/0034068 A1 Feb. 19, 2004

Related U.S. Application Data

(60) Provisional application No. 60/391,886, filed on Jun. 25, 2002.

(30) Foreign Application Priority Data

Jun. 3, 2002 (SE) .................................... 0201669

(51) Int. Cl.
*A61K 31/44* (2006.01)

(52) U.S. Cl. ...................................................... 514/343

(58) Field of Classification Search .................. 514/343
See application file for complete search history.

(56) References Cited

U.S. PATENT DOCUMENTS

| | | | | |
|---|---|---|---|---|
| 3,845,217 A | 10/1974 | Fernö et al. | 426/3 |
| 3,877,468 A | 4/1975 | Lichtneckert et al. | 131/2 |
| 3,901,248 A | 8/1975 | Lichtneckert et al. | 131/2 |
| 4,579,858 A | 4/1986 | Fernö et al. | 514/343 |
| 4,920,989 A | 5/1990 | Rose et al. | 131/270 |
| 4,953,572 A | 9/1990 | Rose et al. | 131/270 |
| 4,967,773 A | 11/1990 | Shaw | 131/359 |
| 5,135,753 A | 8/1992 | Baker et al. | 424/435 |
| 5,167,242 A | 12/1992 | Turner et al. | 131/273 |
| 5,549,906 A | 8/1996 | Santus | 424/440 |
| 5,656,255 A | 8/1997 | Jones | 424/43 |
| 5,709,202 A * | 1/1998 | Lloyd et al. | 128/200.14 |
| 5,713,376 A * | 2/1998 | Berger | 131/270 |
| 5,721,257 A | 2/1998 | Baker et al. | 514/343 |
| 5,810,018 A | 9/1998 | Monte | 131/270 |
| 5,939,100 A | 8/1999 | Albrechtsen et al. | 424/489 |
| 5,955,098 A | 9/1999 | Dugger, III | 424/435 |
| 5,972,974 A * | 10/1999 | Keenan | 514/343 |
| 6,024,097 A | 2/2000 | Von Wielligh | 131/270 |
| 6,413,469 B1 | 7/2002 | Stomp et al. | 266/44 |
| 2002/0017295 A1* | 2/2002 | Weers et al. | 128/203.12 |
| 2003/0159702 A1* | 8/2003 | Lindell et al. | 131/270 |

FOREIGN PATENT DOCUMENTS

| | | |
|---|---|---|
| DE | 32 41 437 | 5/1984 |
| EP | 0148749 * | 7/1985 |
| EP | 0 745 380 A3 | 12/1996 |
| GB | 2 030 862 | 4/1980 |
| GB | 2 289 204 | 11/1995 |
| WO | WO 93/12764 | 7/1993 |
| WO | WO 97/38663 | 10/1997 |
| WO | WO 98/23165 | 6/1998 |
| WO | WO 98/24420 | 6/1998 |
| WO | WO 00/13662 | 3/2000 |
| WO | WO 00/19977 | 4/2000 |
| WO | WO 00/35296 | 6/2000 |
| WO | WO 00/56281 | 9/2000 |
| WO | WO 03/026655 | 4/2003 |
| WO | WO 03/026656 | 4/2003 |
| WO | WO 03/055486 | 7/2003 |

OTHER PUBLICATIONS

Andrus, P.G., et al., "Nicotine microaerosol inhaler," *Can Respir J*, Nov./Dec. 1999, 6(6), 509-512.

Burch, S.G., et al., "Plasma nicotine levels after inhalation of aerosolized nicotine," *Am. Rev. Respir. Dis.*, 1989, 140, 955-957.

Jarvis, M.J., et al., "Nasal nicotine solution as an aid to cigarette withdrawal: a pilot clinical trial," *British Journal of Addiction*, 1987, 82, 983-988.

Molander, L., et al., "Pharmacokinetic investigation of a nicotine sublingual tablet," *Eur. J. Clin. Pharmacol.*, 2001, 56, 813-819.

Rose, J., "Transdermal nicotine as a strategy for nicotine replacement," in The Pharmacological Treatment of Tobacco Dependence: proceedings of the World Congress, *Harvard Univ. Press*, Nov. 4-5, 1985, 158-166.

Russell, M.A.H., et al., "Nasal nicotine solution: a potential aid to giving up smoking?," *British Medical Journal*, Feb. 26, 1983, 286, 683-684.

Russell, M.A.H., et al., "Nicotine boost per cigarette as the controlling factor of intake regulation of smokers," in Effects of Nicotine on Biological Systems II, Advances in Pharmacological Sciences, *Advances in Pharmacological Sciences* , 1995, 233-238.

* cited by examiner

*Primary Examiner*—Jennifer M Kim
(74) *Attorney, Agent, or Firm*—Woodcock Washburn LLP

(57) ABSTRACT

A liquid pharmaceutical formulation comprising nicotine in any form for administration essentially to the lungs being acidified and/or alkalized by buffering and/or pH regulation providing for a $t_{max}$ of nicotine in arterial blood of a subject within a short period of time after administration.

The administration is preferably by spraying an aerosol into the oral cavity for further distribution essentially into the lungs. A method for manufacturing said formulation. Use of said formulation in therapy, such as therapy for treating addiction to tobacco.

47 Claims, No Drawings

FORMULATION AND USE THEREOF

CROSS REFERENCE TO RELATED PATENT APPLICATIONS

The present application is related to and claims priority to U.S. Patent Application Ser. No. (USSN) 60/391,886, filed Jun. 25, 2002 and Swedish Application Serial Number SE 0201669-9, filed Jun. 3, 2002, which are explicitly incorporated herein by reference in their entirety and for all purposes.

FIELD

The present invention relates to liquid pharmaceutical formulations for delivering nicotine to a subject. This invention also relates to methods and systems for delivering nicotine to a subject as well as the manufacturing and use of said liquid pharmaceutical formulations.

BACKGROUND

Tobacco Dependence and Reduction Thereof.

In recent years, with the recognition of the harmful effects of tobacco smoking, there have been numerous campaigns and programs by governmental agencies and various health groups and other interested organizations to disseminate information about the adverse health effects resulting from tobacco smoking. Moreover, and as a result of this recognition of the harmful effects, there have been many programs directed to attempts in reducing smoking incidence.

Nicotine is an organic compound and is the principal alkaloid of tobacco. Nicotine is the chief active ingredient in the tobacco used in cigarettes, cigars, snuff and the like. Nicotine is also an addictive drug, though, and smokers characteristically display a strong tendency to relapse after having successfully stopped smoking for a time. Nicotine is the world's second most used drug, after caffeine from coffee and tea.

The main problem with tobacco smoking is its enormous implications on health. Today it is estimated that smoking-related diseases cause some 3-4 million deaths per year. In the U.S. Surgeon General's 1988 report on The Health Consequences of Smoking, it was estimated that in the U.S. alone about 300.000 deaths are caused each year by diseases related to cigarette smoking. In fact, excessive smoking is now recognized as one of the major health problems throughout the world. This grim consequence of tobacco smoking has urged many medical associations and health authorities to take very strong actions against the use of tobacco.

Even though tobacco smoking is decreasing in many developed countries today it is hard to see how the societies could get rid of the world's second most used drug.

The most advantageous thing a heavy smoker can do is to reduce or preferably even stop smoking completely. Experience shows, however, that most smokers find this extremely difficult since, mostly, tobacco smoking results in a dependence disorder or craving. The WHO has in its International Classification of Disorders a diagnosis called Tobacco Dependence. Others, like the American Psychiatric Association call the addiction Nicotine Dependence. It is generally accepted that these difficulties to stop smoking result from the fact that those heavy smokers are dependent on nicotine. The most important risk factors are, however, substances that are formed during the combustion of tobacco, such as carcinogenic tar products, carbon monoxide, aldehydes, and hydrocyanic acid.

Effects of Nicotine

The administration of nicotine can give satisfaction and the usual method is by smoking, either by smoking e.g., a cigarette, a cigar or a pipe, or by snuffing or chewing tobacco. However, smoking has health hazards and it is therefore desirable to formulate an alternative manner of administering nicotine in a pleasurable manner that can be used to facilitate withdrawal from smoking and/or used as a replacement for smoking.

Upon smoking of a cigarette, nicotine is quickly absorbed into the smoker's blood and reaches the brain within around ten seconds after inhalation. The quick uptake of nicotine gives the consumer a rapid satisfaction, or kick. The satisfaction, then, lasts during the time of smoking the cigarette and for a period of time thereafter. The poisonous, toxic, carcinogenic, and addictive nature of smoking has provided efforts for methods, compositions and devices, which help in breaking the habit of smoking.

Nicotine is an addictive poisonous alkaloid $C_5H_4NC_4H_7NCH_3$, derived from the tobacco plant. Nicotine is also used as an insecticide. Approximately forty milligrams of nicotine may kill an adult (Merck Index).

Nicotine Replacement Products and Prior Art

One way to reduce smoking is to provide nicotine in a form or manner other than by smoking and some products have been developed to fulfill this need. Nicotine containing formulations are currently the dominating treatments for tobacco dependence.

The success in achieving reduction in the incidence of smoking has been relatively poor using presently known products. State of the art involves both behavioral approaches and pharmacological approaches. More than 80% of the tobacco smokers who initially quit smoking after using some behavioral or pharmacological approach to singly reduce smoking incidence generally relapse and return to the habit of smoking at their former rate of smoking within about a one year's period of time.

As an aid for those who are willing to stop smoking there are several ways and forms of nicotine replacement products available on the market, such as nicotine chewing gums according to U.S. Pat. No. 3,845,217. Several methods and means have been described for diminishing the desire of a subject to use tobacco, which comprises the step of administering to the subject nicotine or a derivative thereof as described in e.g. U.S. Pat. No. 5,939,100 (nicotine containing microspheres) and U.S. Pat. No. 4,967,773 (nicotine containing lozenge).

The use of skin patches for transdermal administration of nicotine has been reported (Rose, in Pharmacological Treatment of Tobacco Dependence, (1986) pp. 158-166, Harvard Univ. Press). Nicotine-containing skin patches that are in wide use today can cause local irritation and the absorption of nicotine is slow and affected by cutaneous blood flow.

Nicotine-containing nose drops have been reported (Russell et al., *British Medical Journal*, Vol. 286, p. 683 (1983); Jarvis et al., *British Journal of Addiction*, Vol. 82, p. 983 (1987)). Nose drops, however, are difficult to administer and are not convenient for use at work or in other public situations. Administration of nicotine by way of delivery directly into the nasal cavity by spraying is known from U.S. Pat. No. 4,579,858, DE 32 41 437 and U.S. Pat. No. 5,656,255. There may, though, be local nasal irritation with use of nasal nicotine formulations. The difficulty in administration also results in unpredictability of the dose of nicotine administered.

Mouth sprays comprising nicotine are known in the art, e.g., according to U.S. Pat. No. 6,024,097 wherein is disclosed a method of assisting a smoker in giving up the smoking habit whereby is used a plurality of aerosol dispensers comprising progressively lesser concentrations of nicotine. The aerosol is intended to be administered into the mouth. The liquid in the dispensers essentially consists of nicotine and alcohol. GB 2 030 862 discloses a nicotine-containing aerosol for oral administration.

A similar mouth spray is disclosed in U.S. Pat. No. 5,810,018, whereby in addition the aerosol comprises progressively greater concentrations of at least one selected stimulant.

U.S. Pat. No. 6,413,496 discloses an aerosol device with an active and a propellant. The device may be used for e.g., sublingual administration. Nicotine is mentioned as an active in a long "laundry list" of drugs. There are though no examples on nicotine formulations.

U.S. Pat. No. 5,955,098 discloses a non-polar buccal aerosol spray using a non-polar solvent. Nicotine is mentioned as one useful active in this spray.

Inhaling devices resembling a cigarette are known for uptake of nicotine vapors mainly buccally is suggested in U.S. Pat. No. 5,167,242. A proposal on a nicotine aerosol is disclosed in DE 32 41 437. Newman et al., *J Pharma Sci*, Vol 85, No 9, September 1996 discloses highly ethanolic systems for administering the asthma medication flunisolide as aerosol to the lungs. Possible utility of these systems for delivery of nicotine is though not discussed. Buffering of the medication for facilitating pulmonary delivery is not discussed.

U.S. Pat. No. 4,953,572 and U.S. Pat. No. 4,920,989 disclose one and the same nicotine-containing aerosol intended for inhalation.

Burch et al. disclose in *Am Rev Respir Dis* 189; 140:955-957 pulmonary inhalation of nicotine in conjunction with buccal deposition of a nicotine formulation having pH 10.

Andrus et al. disclose in *Can Respir J* Vol 6 No 6:509-512 a nicotine microaerosol inhaler wherein nicotine is present in a non-pH regulated formulation comprising ethanol and a propellant.

Hitherto is though not known any pharmaceutical formulations or systems that efficiently may administer nicotine for uptake mainly in the lungs in order to mimic the nicotine uptake provided by smoking without the adverse effects caused by smoking.

Problems to be Solved

The captioned means and methods do not satisfy the craving that certain users of tobacco experience. Specifically these means and methods generally do not provide for a sufficiently rapid uptake of nicotine without adverse effects. In nicotine replacement therapy, NRT, many smokers wish to obtain a head rush or very quick onset of nicotine similar to the one obtained by inhaling cigarette smoke. None of hitherto known NRT means may provide for this.

In light of the aforementioned problem there is a strong need and interest to develop formulations, means and methods for the administration of nicotine to provide a very fast satisfaction to a person craving for nicotine or to provide a sense of smoking satisfaction without smoking, whereby also may be avoided problems associated with the prior art means and methods. The present invention addresses said need and interest.

SUMMARY OF THE INVENTION

In view of the foregoing disadvantages known in the art when trying to deliver nicotine to a subject so as to obtain a rapid uptake of nicotine, the present invention provides new and improved products, systems and methods for obtaining a rapid uptake of nicotine essentially in the lungs of the subject.

In contrast to smoking, which involves rapid absorption of nicotine, the use of current nicotine Replacement Therapy (NRT), achieved through use of nicotine formulated in chewing gum, transdermal patch, tablet, nasal spray and inhaler generally provides slower, lower and less variable plasma nicotine concentrations. The arteriovenous differences during cigarette smoking are substantial, with arterial levels exceeding the venous levels six- to ten-fold. The instant relief from craving during cigarette smoking is believed to be achieved by the "nicotine buzz", the sharp rise of nicotine concentration in arterial blood, the arterial blood being transported from the lung alveoli via the heart to the brain within seconds. The nicotine level in the brain declines between cigarettes as the nicotine is distributed to other body tissues. This decline in nicotine level provides an opportunity for resensitization of the nicotine receptors in the brain, allowing some positive reinforcement despite the development of acute tolerance. The current NRT options do not provide this initial sharp rise in arterial blood level. Even if the success rates for smoking cessation with current NRT are twice those obtained using placebo, such therapy is still not very successful. Only up to 30 percent of all people succeed in their attempts to quit smoking. Therefore, there is a strong need, for a more efficient therapy for smoking cessation. This invention provides cigarette-like delivery of nicotine.

Objects of the present invention are to provide an efficient and effective product, as well as methods and systems for an essentially pulmonary uptake of nicotine in a subject to avoid the disadvantages of previously known products and methods.

Thus, the present invention provides a method for delivering nicotine in any form to a subject comprising administering to a subject a liquid pharmaceutical formulation containing nicotine in any form essentially into the lungs of the subject and allowing the nicotine in any form to be absorbed into the systemic circulation of the subject essentially by pulmonary uptake of nicotine as well as a method for manufacturing said liquid pharmaceutical formulation.

The present invention also provides a method for obtaining reduction of the urge to smoke or use tobacco containing material and/or for providing a fast sense of smoking satisfaction without smoking, comprising the steps of replacing some or all of the tobacco containing material with said liquid pharmaceutical formulation, administering to a subject a liquid pharmaceutical formulation containing nicotine in any form essentially to the lungs of the subject and allowing the nicotine to be systemically absorbed by the subject essentially by pulmonary uptake of nicotine.

Furthermore, the present invention provides a system for delivering nicotine in any form to a subject, comprising said liquid pharmaceutical formulation and at least one other means for obtaining reduction of the urge to smoke or use of tobacco as well as a system for obtaining reduction of the urge to smoke or otherwise use of tobacco and/or for providing a sense of smoking satisfaction without smoking, comprising a liquid pharmaceutical formulation as per above and at least one other method for obtaining reduction of the urge to smoke or otherwise use tobacco. Said system may be a system wherein the at least one other method is selected from the group consisting of administration through chewing gums, nasal sprays, mouth sprays, gargles, transdermal patches, lozenges, tablets and parenteral methods, subcutaneous methods, intravenous methods, rectal methods, vaginal methods and transmucosal methods; or other uses of tobacco.

The present invention provides for a flexible, convenient and discrete use in comparison with other means for transmucosal delivery of nicotine, e.g., chewing gums, lozenges, tablets, mouth sprays and other devices attempting to provide nicotine inhalation. No chewing or sucking is necessary. Further, the present liquid pharmaceutical formulation provides nicotine in a form being directly absorbable by a subject. The nicotine in chewing gums, lozenges and tablets need pass a transformation phase, involving e.g., mastication, disintegration, melting and/or dissolution, prior to being present in a directly absorbable form. A nicotine patch provides for a discrete administration, but does not provide for a fast uptake of nicotine. Also, the present invention directly mimics the way a smoker receives nicotine and provides for a head rush and very quick onset of nicotine essentially being the same as experienced with smoking. Therefore a smoker very easily may adapt to using the present invention.

Preferred embodiments of a product according to the present invention is buffered and/or pH regulated in such a way that the pH of the liquid pharmaceutical formulation is from around pH 3 to around pH 7, preferably from around pH 4 to around pH 6.

Use of said product will according to the invention rapidly deliver nicotine in any form to a subject and will also provide for obtaining a quick and/or sustained and/or complete reduction of the urge to smoke or use tobacco and/or for providing a sense of smoking satisfaction without smoking resembling the sense of smoking satisfaction obtained after regular smoking or use of tobacco.

Preferably the present liquid formulation is an ethanol-based formulation or an aqueous-based formulation. Principally these respective formulations are manufactured as follows:

Ethanol-Based Formulation:

Take the required amount of ethanol.

Add the required amount of water.

Add the required amount of propylene glycol and/or glycerol.

Add the required amount of organic and/or inorganic acid.

Mix the ingredients until homogeneous.

Add the required amount of nicotine or nicotine in salt form.

Optionally add further ingredients

Mix the ingredients until homogeneous.

Adjust apparent pH, targeting 3.0 to 5.5.

All operations may be done at room temperature and no other ingredients, such as preservatives, are required.

Aqueous-Based Formulation:

Take the required amount of water.

Add the required amount of salt, e.g., sodium chloride.

Add the required amount of organic and/or inorganic acid.

Mix the ingredients until homogeneous.

Add the required amount of preservative, such as benzalkonium chloride.

Add the required amount of nicotine or nicotine in salt form.

Optionally add further ingredients

Mix the ingredients until homogeneous.

Adjust pH, targeting 5.5 to 7.0.

All operations may be done a room temperature.

The buffering agent and the pH regulating means

In a preferred embodiment of the present invention, the composition of the liquid has its pH adjusted to between 3 and 7. Thereby the pH is close to the physiological pH without causing significant irritation. As the pKa for the acid dissociation constant of the mono protonated form of nicotine in an aqueous system is approximately 8.0 at 20° C., at pH's in the range 5 to 7 virtually all of the nicotine (90% to 99.9%) exists in its mono protonated form and is thereby prevented from existing in the vapor phase. For the ethanol-based system the apparent pKa is approximately 6.5 at 20° C. and, consequently, at apparent pHs in the range 3 to 5.5 virtually all of the nicotine (90% to 99%) exists in its mono-protonated form and is thereby prevented from existing in the vapor phase.

Hence and according to the invention, the liquid pharmaceutical formulation is acidified and/or alkalized by buffering and/or pH regulation. This may be achieved by including physiologically acceptable buffering substances or agents, or by other means. With other means it is intended to include buffering by any component in the product, which may not normally act as a buffering agent, such as a self-buffering additive and/or pH regulating forms of nicotine. Accordingly, for use in the present invention, the terms "buffering agent" and "pH regulating agent" may include any agent capable of regulating pH.

In some embodiments of the present invention, buffering and/or pH regulation decreases the pH of the pharmaceutical formulations of the present invention thereby causing uptake of nicotine to take place mainly in the lungs rather than in the oral cavity or in the respiratory tract. Hence, only small amounts of nicotine are swallowed and reach the gastrointestinal (GI) tract. Nicotine that reaches the GI tract will be subjected to first pass metabolism, which reduces the total amount of intact nicotine absorbed. This means that the bioavailability of nicotine that is not co-administered with a buffer according to the invention will generally be lower than when administered together with a buffer.

A titration curve for nicotine with sulphuric acid in a 90:10 ethanol:water matrix shows that the apparent pKa of nicotine in 90% ethanol is 6.5. This means that at apparent pH 6.5, 50% of the nicotine is in its free base form. Separately, an Andersen Cascade Impactor (ACI) experiment, performed with a formulation at an apparent pH=4.0, demonstrated that nicotine (in its salt form at this apparent pH) remains in the liquid droplets. The majority of the droplets has sizes less than 3.3 microns and would be deposited in the lungs upon inhalation. By comparison, an ACI experiment, performed with a formulation at an apparent pH=6.0, demonstrated that part of the nicotine (approximately 15% of it is in its free base form at this apparent pH) escapes from the liquid droplets as a vapor. It is well known that inhaled nicotine vapor deposits in the oral cavity. Therefore, the nicotine in its base form, inhaled in this formulation would not be deposited in the lungs.

In conclusion, the above set of experiments demonstrates the utility of the present invention for delivering nicotine to the lungs.

An acidifying effect may be achieved by the use of one or more buffering agents selected from the group consisting of citric acid, phosphoric acid, acetic acid, hydrochloric acid, nitric acid, sulphuric acid and acidic salts thereof.

An alkalizing effect may be achieved by the use of one or more buffering agents selected from the group consisting of a carbonate, such as mono-carbonate, bicarbonate or sesquicarbonate; glycinate, phosphate, glycerophosphate, acetate, gluconate or citrate of an alkali metal, such as potassium or sodium, or of ammonium, and mixtures thereof; and/or by the use of pH regulating agents, such as agents selected from the group consisting of sodium hydroxide, potassium hydroxide, calcium hydroxide and calcium oxide; and/or by using at least partly pH regulating forms of nicotine.

The pH regulation may also be obtained by using pH-regulating forms of nicotine, e.g., nicotine free base.

The nicotine may be administered in different forms, e.g., in different complexes or salts or as free base.

DETAILED DESCRIPTION

The terms "tobacco", "tobacco containing material" and similar are herein intended to mean such material for any type of use of tobacco including smoking, snuffing or chewing whereby is used inter alia a cigarette, a cigar, pipe tobacco, snuff and chewing tobacco.

The term "fast reduction of the urge to smoke or use tobacco" is herein intended to mean an initial priming of the subject so as to achieve a reduction of the urge to smoke or use tobacco.

The term "buccal" and "buccally" are herein intended to pertain to all of or any part of the soft tissue lining of the oral cavity.

The term "pulmonary uptake" is herein intended to mean that the active agent passes the lung tissue whereupon it enters the systemic circulation.

The term "delivery to the lungs" or "administration to the lungs" and similar is herein intended to mean deposition of an active agent on lung tissue.

The term "incidence of administration" is herein intended to mean administration of one or more single doses of the liquid pharmaceutical formulation within the same time frame, said time frame being dependent on the needs of the subject receiving the administration, said time frame extending from a few seconds to around ten minutes.

The Active Ingredient

According to the invention, the liquid pharmaceutical formulation product comprises nicotine in any form to provide an essentially pulmonary uptake of the nicotine so as to obtain a rapid "nicotine kick or buzz" or "nicotine head rush" or reduction of the urge to smoke and/or use tobacco. Thereby may also be achieved a systemic maintenance level of nicotine.

The nicotine should be in a form facilitating the uptake of the nicotine in the lungs.

The nicotine may act as a stimulant to e.g., obtain a rapid reduction of the urge to smoke or to use tobacco.

With nicotine it is intended to include nicotine, 3-(1-methyl-2-pyrrolidinyl)pyridine, including the racemate and the enantiomers, with its base form, including synthetic nicotine as well as nicotine extracts from tobacco plants, or parts thereof, such as the genus Nicotiana alone or in combination; or pharmaceutically acceptable salts. In some embodiments of the present invention, the term nicotine also includes nicotine derivatives, such as nicotine metabolites, e.g., cotinine.

In preferred embodiments, the nicotine in any form is selected from the group consisting of the free base form of nicotine or a nicotine salt.

Preferred nicotine salts are salts with the following acids, Formic, Acetic, Propionic, Butyric, 2-Methylbutyric, 3-Methylbutyric, Valeric, Lauric, Palmitic, Tartaric, Citric, Malic, Oxalic, Benzoic, Gentisic, Gallic, Phenylacetic, Salicylic, Phthalic, Picric, Sulfosalicylic, Tannic, Pectic, Alginic, Hydrochloric, Chloroplatinic, Silicotungstic, Pyruvic, Glutamic and/or Aspartic.

Most preferred nicotine salts are tartrate, hydrogen tartrate, citrate and malate.

The most preferable embodiment incorporates nicotine as the free base form or as a water-soluble pharmaceutically acceptable salt.

According to the invention, the uptake of the nicotine in the lungs is improved in relation to the lung uptake obtained by pulmonary administration of a theoretical liquid pharmaceutical formulation devoid of buffering agents or devoid of pH-regulating means.

Amount of the Nicotine in the Liquid Pharmaceutical Formulation

The nicotine in any form is according to the invention formulated to provide the subject with a dose to achieve an effect. The effect may be to provide a sense of smoking satisfaction without smoking. Another effect of the administered nicotine in any form may be a reduction of the urge to smoke or use tobacco.

The effect may also be a combination of a reduction of said urge and providing a sense of smoking satisfaction without smoking. The amount of the nicotine should be sufficient to provide such an effect in a subject. This amount may, of course, vary from person to person.

According to the invention, embodiments of the liquid pharmaceutical formulation comprise nicotine in such concentrations that the amount of nicotine delivered at each incidence of administration is about 0.05-10 mg calculated as the free base form of nicotine, preferably about 0.5-5 mg and most preferably about 0.5-1 mg.

Release and Uptake of Nicotine

The time point for reaching a sense of satisfaction or reduction of urge to smoke or use tobacco after administration is individual, but may in existing pharmaceutical forms for administering nicotine generally be reached after approximately 30 minutes when regarded as coinciding with $t_{max}$. According to the present invention, such a sense of satisfaction may be reached after a shorter period of time due to a rapid transmucosal uptake in the lungs due to the buffering and/or pH regulation and due to the absence of rate-limiting steps, such as tablet or lozenge melting, tablet or lozenge disintegration and dissolution and chewing gum mastication, followed by drug dissolution.

As used herein, "$t_{max}$" is the time to reach maximum concentration of nicotine in the blood of a subject following administration of a single dosage of nicotine to the subject.

The Liquid Phase

The liquid phase of the present liquid pharmaceutical formulation may comprise water. The liquid phase may also comprise an alcohol, such as ethanol, glycerol, propylene glycol and polyethylene glycol, or mixtures thereof. Further it may comprise mixtures of the above ingredients.

One or more of the compounds of the liquid pharmaceutical formulation may be solubilized in one or more surface active agents and/or emulsifiers, such as nonionic, cationic, anionic or zwitterionic surfactants, including amphiphilic block copolymers, or mixtures thereof.

Other Additives to the Liquid Pharmaceutical Formulation

Other additives may be added optionally to the liquid pharmaceutical formulation. These include tonicity agents, preferably chosen from sugars and inorganic salts.

Method for Delivering Nicotine in Any Form to a Subject

According to the invention, a method for delivering nicotine in any form to a subject comprises the steps of:

a) administering to a subject a liquid pharmaceutical formulation product containing nicotine in any form according to the invention for delivery into the lungs of the subject, and b) allowing the nicotine in any form in the liquid pharmaceutical formulation to be absorbed into the blood plasma of the subject essentially by pulmonary uptake.

One embodiment results in a $t_{max}$ of nicotine in arterial blood of the subject in less than about 10 minutes.

A further embodiment results in a $t_{max}$ of nicotine in arterial blood of the subject in less than 3 minutes and less than 1 minute.

In still one further embodiment, said nicotine in any form is absorbed resulting in a $t_{max}$ of nicotine in venous blood of the subject in less than 20 minutes, preferably in less than 15 minutes.

Method for Obtaining Reduction of the Urge to Smoke or to Use Tobacco

A method for obtaining reduction of the urge to smoke or use tobacco-containing material and/or for providing a sense of smoking satisfaction without smoking according to the invention comprises the steps of:

a) replacing at least partly the tobacco containing material with a liquid pharmaceutical formulation according to the present invention, b) administering to a subject a liquid pharmaceutical formulation containing nicotine in any form according to the present invention for delivery essentially to the lungs of the subject, and c) allowing the nicotine in any form in the liquid pharmaceutical formulation to be absorbed by the subject essentially by pulmonary uptake.

The Administration to the Lungs Preferably Takes Place by Aerosolization.

Aerosolization is preferably achieved by use of a nebulizer. For conventional nebulizers, the nicotine is dissolved in a solution, see above, and the drug solution is placed in the nebulizer cup. A high velocity air stream is passed over a capillary tube extending into the drug solution. The low pressure created by this jet stream draws the liquid into the jet stream. Internal baffling creates a standing aerosol cloud from which the subject receives the dose upon inhalation. The remainder of the aerosol is recycled within the nebulizer.

Recently, portable nebulizers, often times referred to as Air Mist Inhalers or AMIs, have emerged. These devices generate the standing aerosol cloud by various techniques such as ultrasonic methods, mechanical break-up and electrohydrodynamics. These AMIs overcome most of the drawbacks of conventional nebulizers (bulky size, need for an external power source, low efficiency, long treatment times, etc.). One such AMI is disclosed in *Am Rev Respir Dis* 1989; 140: 955-957. More efficient AMIs are envisageable.

In one embodiment said nicotine in any form reaches a $t_{max}$ of nicotine in arterial blood of the subject in less than 10 minutes irrespective of the dose of nicotine.

In further embodiments said nicotine in any form reaches a $t_{max}$ of nicotine in arterial blood of the subject in less than 3 minutes or less than 1 minute irrespective of the dose of nicotine.

In still one further embodiment said nicotine in any form reaches a $t_{max}$ of nicotine in venous blood of the subject in less than 20 minutes, preferably in less than 15 minutes, irrespective of the dose of nicotine.

Even further embodiments of the method for delivering nicotine to a subject may comprise the steps of combining at least one other method for obtaining reduction of the urge to smoke or use of tobacco.

The liquid pharmaceutical formulation may be used for obtaining a quick and/or sustained and/or complete reduction of the urge to smoke or use tobacco and/or for providing a sense of smoking satisfaction without smoking as further discussed below.

The fast relief provides the subject with a sense of rapid smoking satisfaction without smoking.

One embodiment reduces the urge to smoke or use of tobacco by reaching a $t_{max}$ of nicotine in arterial blood of the subject in less than 10 minutes by the use of a liquid pharmaceutical formulation according to the invention.

Further embodiments reduce the urge to smoke or use tobacco by reaching a $t_{max}$ of nicotine in arterial blood of the subject in less than 3 minutes or less than 1 minute by the use of a liquid pharmaceutical formulation according to the invention.

Still one further embodiment reduces the urge to smoke or use tobacco by reaching a $t_{max}$ of nicotine in venous blood of the subject in less than 20 minutes, preferably in less than 15 minutes by the use of a liquid pharmaceutical formulation according to the invention.

Cessation of the Urge to Smoke or Use Tobacco

For some of the users, it may be a goal to terminate the usage of nicotine completely, due to several reasons e.g., health, economical, social or behavioral. This may be achieved by further decreasing the delivered amount of nicotine in any form gradually over time. In specific embodiments of the invention, the method described above for obtaining craving relief may further comprise the steps of decreasing the amount of nicotine in the liquid pharmaceutical formulation gradually over time, and/or the steps of reducing the incidence of administration of the liquid pharmaceutical formulation gradually over time, and/or the steps of reducing the dosage size of the liquid pharmaceutical formulation gradually over time, so as to achieve a relief of tobacco craving and/or to achieve a sense of smoking satisfaction. This method results in a weaning process gradually over time.

Different types of smokers reach the sense of reduced craving at different plasma levels of nicotine. This may, of course, affect the individual types of programs for administering a liquid pharmaceutical formulation according to the invention. Different types of smokers include e.g., peak seekers or smokers that crave for a plasma level of nicotine constantly being above the level below which withdrawal symptoms occur.

One strategy may be to lower the frequency of administering the liquid pharmaceutical formulation. Other embodiments include varying the dose of the nicotine in said liquid pharmaceutical formulation as well as the combination of these two embodiments.

Systems for Delivering Nicotine and for Obtaining Craving Relief

According to the invention there is a system for delivering nicotine in any form to a subject. Such a system comprises a liquid pharmaceutical formulation according to the invention and at least one other means for obtaining reduction of the urge to smoke.

Another system according to the invention may be a system for obtaining reduction of the urge to smoke or use tobacco and/or for providing a sense of smoking satisfaction without smoking. Such a system comprises a liquid pharmaceutical formulation according to the invention and at least one other method for obtaining reduction of the urge to smoke or use tobacco. Other methods may be a concomitant or concurrent method selected from the group consisting of administration through chewing gums, nasal sprays, transdermal patches, mouth sprays, lozenges, tablets and parenteral methods, subcutaneous methods, intravenous methods, rectal methods, vaginal methods and transmucosal methods; or use of tobacco.

In a specific embodiment, the at least one other method comprises administration of nicotine.

Use of the Liquid Pharmaceutical Formulation

The use of the liquid pharmaceutical formulation according to the invention is for obtaining a fast and/or sustained and/or complete reduction of the urge to smoke and use tobacco or for providing a sense of smoking without smoking as described above.

The dose of the nicotine is chosen to give the subject an individual sensory perception and satisfaction with an effect of the nicotine in any form. The use of the liquid pharmaceutical formulation may also be a sole use according to the invention or a combination with other means or methods known in the field of drug abuse. Specifically, the present invention may be used in combination with other means as described above in the methods in the paragraphs above.

The use may give a quick reduction of the urge to smoke or use tobacco whereby is reached a $t_{max}$ of nicotine in arterial blood in less than about 10 minutes.

In other embodiments, the use of the liquid pharmaceutical formulation according to the invention will reduce the urge to smoke or use tobacco by reaching a $t_{max}$ of nicotine in arterial blood of the subject in less than about 3 minutes or in less than about 1 minute.

In a further embodiment, the use of the liquid pharmaceutical formulation according to the invention will reduce the urge to smoke or use tobacco by reaching a $t_{max}$ of nicotine in venous blood of the subject in less than about 20 minutes, preferably in less than about 15 minutes.

According to the invention, a use of a liquid pharmaceutical formulation according to the invention is for delivering nicotine in any form to a subject.

In different embodiments, the delivering of nicotine in any form results in a $t_{max}$ of nicotine in arterial blood of the subject in less than about 10 minutes, in less than about 3 minutes and/or in less than about 1 minute, and/or results in a $t_{max}$ of nicotine in venous blood of the subject in less than about 20 minutes, preferably in less than about 15 minutes.

Use for Therapy, Treatment and Manufacturing

The liquid pharmaceutical formulation product according to the invention may be used in therapy. Said therapy may be a treatment of a disease or medical indication selected from the group consisting of reduction in use of tobacco, cessation of use of tobacco, other use of tobacco, temporary abstinence from abstaining from use of tobacco, Alzheimer's disease, Crohn's disease, Parkinson's disease, Tourette's syndrome, and ulcerative colitis; and weight control.

Nicotine in any form may be used for the manufacturing of a liquid pharmaceutical formulation according to the invention for the treatment of a disease or medical indication selected from the group consisting of reduction in use of tobacco, cessation of use of tobacco, other use of tobacco, temporary abstinence from abstaining from using tobacco, Alzheimer's disease, Crohn's disease, Parkinson's disease, Tourette's syndrome, and ulcerative colitis; and weight control.

A liquid pharmaceutical formulation comprising nicotine in any form for administration essentially to the lungs being acidified and/or alkalized by buffering and/or pH regulation providing for a $t_{max}$ of nicotine in arterial blood of a subject within a short period of time after administration.

The administration is preferably by spraying an aerosol into the oral cavity for further distribution essentially into the lungs. A method for manufacturing said formulation. Use of said formulation in therapy, such as therapy for treating addiction to tobacco.

All publications and patent documents cited above are hereby incorporated by reference in their entirety for all purposes to the same extent as if each were so individually denoted.

EXAMPLES

The below examples are non-limiting and for illustrating the present invention. Alternatives and variations of the below examples within the scope of the present invention as per the below claims may be carried out by a person skilled in the art. Ingredients as per the below examples may be exchanged for equivalent ingredients, preferably as per above.

As stated under the captioned Summary of the invention the present liquid pharmaceutical formulation is preferably an ethanol- or an aqueous-based formulation in principle being manufactured as follows:

Ethanol-Based Formulation:

Take the required amount of ethanol.

Add the required amount of water.

Add the required amount of propylene glycol and/or glycerol.

Add the required amount of organic acid and/or inorganic acid.

Mix the ingredients until homogeneous.

Add the required amount of nicotine as free base or nicotine in salt form.

Optionally add further ingredients.

Mix the ingredients until homogeneous.

Adjust apparent pH, targeting 3.0 to 5.5.

All operations may be done at room temperature and no other ingredients, such as preservatives, are required.

Aqueous-Based Formulation:

Take the required amount of water.

Add the required amount of salt, e.g., sodium chloride.

Add the required amount of organic and/or inorganic acid.

Mix the ingredients until homogeneous.

Add the required amount of preservative, such as benzalkonium chloride.

Add the required amount of nicotine as free base or nicotine in salt form.

Optionally add further ingredients

Mix the ingredients until homogeneous.

Adjust pH, targeting 5.5 to 7.0.

All operations may be done at room temperature.

The present liquid pharmaceutical formulation is not limited to the above embodiments or to the below Examples.

Example 1

Manufacturing of 100 ml ethanol-based formulation with 10 μg nicotine/μl and pH around 3.0.

60 g 99% ethanol and 9.9 g (polyethylene) propylene glycol was thoroughly mixed with 1000 mg nicotine at room temperature. Thereafter pH was adjusted to 3.0 using diluted sulphuric acid. Thereafter the volume was adjusted to 100.0 ml with addition of 99% ethanol. The solution was aseptically filtered and put into appropriate sterile container.

Example 2

Manufacturing of 100 ml ethanol-based formulation with 10 μg nicotine/μl and pH around 4.0.

60 g 99% ethanol and 9.9 g (polyethylene) propylene glycol was thoroughly mixed with 1000 mg nicotine at room temperature. Thereafter pH was adjusted to 4.0 using diluted HCl. Thereafter the volume was adjusted to 100.0 ml with addition of 99% ethanol. The solution was aseptically filtered and put into appropriate sterile container.

Example 3

Manufacturing of 100 ml ethanol-based formulation with 50 μg nicotine/μl and pH around 5.0.

60 g 99% ethanol and 9.9 g (polyethylene) propylene glycol was thoroughly mixed with 5000 mg nicotine at room temperature. Thereafter pH was adjusted to 5.0 using diluted sulphuric acid. Thereafter the volume was adjusted to 100.0 ml with addition of 99% ethanol. The solution was aseptically filtered and put into appropriate sterile container.

Example 4

Manufacturing of 100 ml ethanol-based formulation with 50 μg nicotine/μl and pH around 5.5.

60 g 99% ethanol and 9.9 g glycerol was thoroughly mixed with 5000 mg nicotine at room temperature. Thereafter pH was adjusted to 5.5 using diluted sulphuric acid. Thereafter the volume was adjusted to 100.0 ml with addition of 99% ethanol. The solution was aseptically filtered and put into appropriate sterile container.

Example 5

Manufacturing of 100 ml aqueous-based formulation with 10 μg nicotine/μl and pH around 5.0.

60 g distilled water, 0.9 g sodium chloride and 100 mg citric acid was thoroughly mixed with 1000 mg nicotine at room temperature. Thereafter pH was adjusted to 5.0 using 0.1% citric acid. Thereafter the volume was adjusted to 100.0 ml with addition of distilled water. The solution was aseptically filtered and put into appropriate sterile container.

Example 6

Manufacturing of 100 ml aqueous-based formulation with 10 μg nicotine/μl and pH around 7.0.

60 g distilled water and 0.9 g sodium chloride was thoroughly mixed with 1000 mg nicotine at room temperature. Thereafter pH was adjusted to 7.0 using 0.1% citric acid. Thereafter the volume was adjusted to 100.0 ml with addition of distilled water. The solution was aseptically filtered and put into appropriate sterile container.

Example 7

Manufacturing of 100 ml aqueous-based formulation with 50 μg nicotine/μl and pH around 5.0.

60 g distilled water, 0.9 g sodium chloride and 100 mg citric acid was thoroughly mixed with 5000 mg nicotine at room temperature. Thereafter pH was adjusted to 5.0 using diluted HCl. Thereafter the volume was adjusted to 100.0 ml with addition of distilled water. The solution was aseptically filtered and put into appropriate sterile container.

Example 8

Manufacturing of 100 ml aqueous-based formulation with 50 μg nicotine/μl and pH around 6.0.

60 g water, 0.9 g sodium chloride and 100 mg citric acid was thoroughly mixed with 5000 mg nicotine at room temperature. Thereafter pH was adjusted to 6.0 with diluted HCl. Thereafter the volume was adjusted to 100.0 ml with addition of distilled water. The solution was aseptically filtered and put into appropriate sterile container.

Example 9

Manufacturing of 100 ml aqueous-based formulation with 10 μg nicotine/μl and pH around 5.0.

60 g distilled water, 0.9 g sodium chloride and 100 mg citric acid was thoroughly mixed with 3072 mg nicotine hydrogen tartrate at room temperature. Thereafter pH was adjusted to 5.0 using diluted HCl. Thereafter the volume was adjusted to 100.0 ml with addition of distilled water. The solution was aseptically filtered and put into appropriate sterile container.

Example 10

Manufacturing of 100 ml aqueous-based formulation with 50 μg nicotine/μl and pH around 6.0.

60 g water, 0.9 g sodium chloride and 100 mg citric acid was thoroughly mixed with 15.362 g nicotine hydrogen tartrate at room temperature. Thereafter pH was adjusted to 6.0 using diluted HCl. Thereafter the volume was adjusted to 100.0 ml with addition of distilled water. The solution was aseptically filtered and put into appropriate sterile container.

The liquid pharmaceutical formulation may within the inventive concept comprise ingredients in other amounts than in the above examples.

Hence the liquid pharmaceutical formulation may be essentially alcohol-based, whereby it comprises nicotine in any form, at least 50%, preferably at least 90% and most preferably around 99% alcohol, preferably ethanol, one or more buffering agents, and optionally propylene glycol, one or more organic or inorganic acids, and other additives.

Also the liquid pharmaceutical formulation may be essentially water-based, whereby it comprises nicotine in any form, at least 50%, preferably at least 90% and most preferably at least 99% water, one or more buffering agents, and optionally one or more preservatives and other additives.

Further, also other percentage ranges are within the inventive concept.

We claim:

1. A pharmaceutical aerosol formulated for administration to a subject's lungs comprising liquid droplets less than 3.3 microns in size, said liquid droplets comprising un-complexed nicotine, a buffering or pH regulating agent in an amount sufficient to adjust the pH of the formulation to an apparent pH in the range of 3 to 5.5, and at least 50% alcohol by weight, wherein at least 90% of said nicotine exists in a mono-protonated form and is thereby prevented from existing in the vapor phase.

2. The pharmaceutical aerosol of claim 1, wherein said aerosol, following administration to said lungs yields a tmax of nicotine in the arterial blood of said subject in less than about 10 minutes.

3. The pharmaceutical aerosol of claim 1, wherein said buffering agent is selected from the group consisting of citric acid, phosphoric acid, acetic acid, hydrochloric acid, nitric acid, sulphuric acid and acidic salts thereof.

4. The pharmaceutical aerosol of claim 1, wherein said buffering agent is selected from the group consisting of a carbonate, a glycinate, a phosphate, a glycerophosphate, an acetate, a gluconate, and a citrate.

5. The pharmaceutical aerosol of claim 4, wherein said carbonate is a mono-carbonate, a bicarbonate or a sesquicarbonate.

6. The pharmaceutical aerosol of claim 4, wherein said citrate is a citrate of an alkali metal or of ammonium or mixtures thereof.

7. The pharmaceutical aerosol of claim 6, wherein said alkali metal is sodium or potassium.

8. The pharmaceutical aerosol of claim 1, wherein said pH regulating agent is selected from the group consisting of sodium hydroxide, potassium hydroxide, calcium hydroxide, calcium oxide, and pH regulating forms of nicotine.

9. The pharmaceutical aerosol of claim 1, wherein said liquid droplets have an acidic pH and said buffering or pH regulating agent is selected from the group consisting of citric acid, phosphoric acid, acetic acid, hydrochloric acid, nitric acid, sulphuric acid, acidic salts thereof, and partly pH regulating forms of nicotine.

10. The pharmaceutical aerosol of claim 1, wherein said nicotine is present as a free base, a nicotine salt, a nicotine metabolite, or combinations thereof.

11. The pharmaceutical aerosol of claim 10, wherein said nicotine metabolite is cotinine.

12. The pharmaceutical aerosol of claim 10, wherein said nicotine salt is a salt formed as tartrate, hydrogen tartrate, citrate, sulphate or malate.

13. The pharmaceutical aerosol of claim 1, wherein the amount of nicotine administered to the lungs is about 0.05-10 mg calculated as the free base form of nicotine.

14. The pharmaceutical aerosol of claim 13, wherein the amount of nicotine administered to the lungs is about 0.5-5 mg calculated as the free base form of nicotine.

15. The pharmaceutical aerosol of claim 14, wherein the amount of nicotine administered to the lungs is about 0.5-1 mg calculated as the free base form of nicotine.

16. The pharmaceutical aerosol of claim 1, wherein said liquid droplets further comprise water.

17. The pharmaceutical aerosol of claim 1, wherein said alcohol is ethanol, glycerol, propylene glycol, polyethylene glycol, or mixtures thereof.

18. The pharmaceutical aerosol of claim 17, wherein said alcohol is ethanol.

19. The pharmaceutical aerosol of claim 1, wherein said formulation comprises water and an alcohol.

20. The pharmaceutical aerosol of claim 1, further comprising a surface active agent or an emulsifier.

21. The pharmaceutical aerosol of claim 20, wherein said surface active agent or emulsifier is selected from the group consisting of nonionic, cationic, anionic and zwitterionic surfactants.

22. The pharmaceutical aerosol of claim 21, wherein said surface active agent or emulsifier is selected from the group consisting of amphiphilic block copolymers and mixtures thereof.

23. The pharmaceutical aerosol of claim 1, wherein said liquid droplets further comprise water and sodium chloride; and wherein said alcohol is ethanol.

24. The pharmaceutical aerosol of claim 23, wherein said formulation further comprises sodium hydroxide, hydrochloric acid or mixtures thereof.

25. The pharmaceutical aerosol of claim 1, wherein said formulation further comprises one or more tonicity agents.

26. The pharmaceutical aerosol of claim 25, wherein said tonicity agent is selected from the group consisting of sugars and inorganic salts.

27. The pharmaceutical aerosol of claim 1, wherein said liquid droplets comprise at least 90% alcohol by weight.

28. The pharmaceutical aerosol of claim 27, wherein said liquid droplets comprise at least around 99% alcohol by weight.

29. The pharmaceutical aerosol of claim 1, wherein said alcohol is ethanol and said liquid droplets further comprise propylene glycol.

30. A method for delivering nicotine to a subject, the method comprising the steps of:

(a) administering the pharmaceutical aerosol of claim 1 into the lungs of the subject in need thereof, and (b) allowing the nicotine to be systematically absorbed by pulmonary uptake of nicotine.

31. The method of claim 30, wherein absorption of said nicotine yields a tmax of nicotine in arterial blood of the subject in less than about 10 minutes.

32. The method of claim 31, wherein absorption of said nicotine yields a tmax of nicotine in arterial blood of the subject in less than about 3 minutes.

33. The method of claim 32, wherein absorption of said nicotine yields a tmax of nicotine in arterial blood of the subject in less than about 1 minute.

34. The method of claim 30, wherein absorption of said nicotine yields a tmax of nicotine in venous blood of the subject in less than about 20 minutes.

35. The method of claim 34, wherein absorption of said nicotine yields a tmax of nicotine in venous blood of the subject in less than about 15 minutes.

36. A method for obtaining reduction of the urge to use tobacco containing material in a subject in need thereof, the method comprising the steps of:

(a) replacing some or all of the tobacco containing material used by a subject with the pharmaceutical aerosol of claim 1;

(b) administering the pharmaceutical aerosol of claim 1 into the lung cavity of the subject; and (c) allowing the nicotine to be systematically absorbed by the subject by pulmonary uptake.

37. The method of claim 36, wherein said method reduces the urge to smoke in the subject.

38. The method of claim 36, wherein said method provides a sense of smoking satisfaction without smoking.

39. The method of claim 36, wherein absorption of said nicotine yields a tmax of nicotine in arterial blood of the subject in less than about 10 minutes.

40. The method of claim 39, wherein absorption of said nicotine yields a tmax of nicotine in arterial blood of the subject in less than about 3 minutes.

41. The method of claim 40, wherein absorption of said nicotine yields a tmax of nicotine in arterial blood of the subject after about 1 minute.

42. The method of claim 36, wherein absorption of said nicotine yields a tmax of nicotine in venous blood of the subject in less than about 20 minutes.

43. The method of claim 42, wherein absorption of said nicotine yields a tmax of nicotine in venous blood of the subject in less than about 15 minutes.

44. The method of claim 36, wherein the said pharmaceutical aerosol is administered by spraying said aerosol into the oral cavity for further delivery into the lungs.

45. The method of claim 36, wherein the method for obtaining reduction of the urge to use tobacco containing material is performed in combination with one or more additional methods for obtaining reduction of the urge to use tobacco containing material.

46. The method of claim 45, wherein the method for obtaining reduction of the urge to use tobacco containing material is performed in combination with the administration of nicotine through chewing gums, nasal sprays, transdermal patches, mouth sprays, lozenges, tablets, parenteral means, subcutaneous means, intravenous means, rectal means, vaginal means, transmucosal means, or tobacco.

47. The pharmaceutical aerosol of claim 1, wherein said liquid droplets further comprise water;

wherein said alcohol is a mixture of ethanol and at least one of propylene glycol or glycerol; and wherein said buffering agent or pH regulating agent is an acid.

* * * * *